United States Patent [19]

Yatabe

[11] 4,378,210
[45] Mar. 29, 1983

[54] EXTRAORAL ANCHORAGE DEVICE FOR USE IN ORTHOPEDICS

[75] Inventor: Kenichi Yatabe, Tokyo, Japan

[73] Assignee: Clarion Co., Ltd., Tokyo, Japan

[21] Appl. No.: 100,300

[22] Filed: Dec. 5, 1979

Related U.S. Application Data

[63] Continuation-in-part of Ser. No. 789,728, Apr. 21, 1977, abandoned, which is a continuation-in-part of Ser. No. 587,058, Jun. 16, 1975, abandoned.

[51] Int. Cl.$^3$ .............................................. A61C 3/00
[52] U.S. Cl. ........................................... 433/5; 433/17
[58] Field of Search .............................. 433/5, 17, 20

[56] References Cited

U.S. PATENT DOCUMENTS

| | | | |
|---|---|---|---|
| 1,085,466 | 1/1914 | Montag | 433/12 |
| 1,322,994 | 11/1919 | Angle | 433/14 |
| 1,398,761 | 11/1921 | Angle et al. | 433/17 |
| 1,849,843 | 3/1932 | Levin | 433/20 |
| 3,087,245 | 4/1963 | Asher | 433/5 |
| 3,121,953 | 2/1964 | Asher | 433/5 |
| 3,186,089 | 1/1965 | Asher | 433/5 |
| 3,494,034 | 2/1970 | Kesling | 433/23 |
| 3,815,238 | 6/1974 | Wallshein | 433/5 |
| 3,903,604 | 9/1975 | Snead | 433/5 |
| 3,916,526 | 11/1975 | Schudy | 433/17 |

Primary Examiner—Gene Mancene
Assistant Examiner—John J. Wilson
Attorney, Agent, or Firm—Wallenstein, Wagner, Hattis, Strampel & Aubel

[57] ABSTRACT

An extraoral anchorage device for imparting orthopedic force to teeth is provided which comprises outer bows for transmitting an external force to teeth and inner bows for transmitting the force delivered by the outer bows to buccal tubes respectively fixed to said teeth, said inner bows being connected to the outer bows and having outer free ends. In the extraoral anchorage device the improvement consists in that the outer free ends of said inner bows have a non-circular cross section. By the use of the extraoral anchorage device according to the present invention, the orthopedic force is transmitted from the outer free ends of the inner bows to the buccal tubes without rotational movement.

2 Claims, 10 Drawing Figures

EXTRAORAL ANCHORAGE DEVICE FOR USE IN ORTHOPEDICS

CROSS-REFERENCE TO RELATED APPLICATION

This application is a continuation-in-part of application Ser. No. 789,728 filed on Apr. 21, 1977, now abandoned, which is a continuation-in-part of Ser. No. 587,058, filed on June 16, 1975, and now abandoned.

BACKGROUND OF THE INVENTION

This invention relates to an anchoring device for use in orthopedic practice.

In general, such anchoring device has been used to reform molars and maxillary bone in relation to a face bow.

It is an object of this invention to provide an improved anchoring device wherein the traction force for the face bow can be effectively used for orthopedic purpose.

Another object is to provide an improved anchoring device wherein a correctly controlled force can be used for orthopedic purpose.

DESCRIPTION OF THE PREFERRED EMBODIMENTS

Figure 1A:
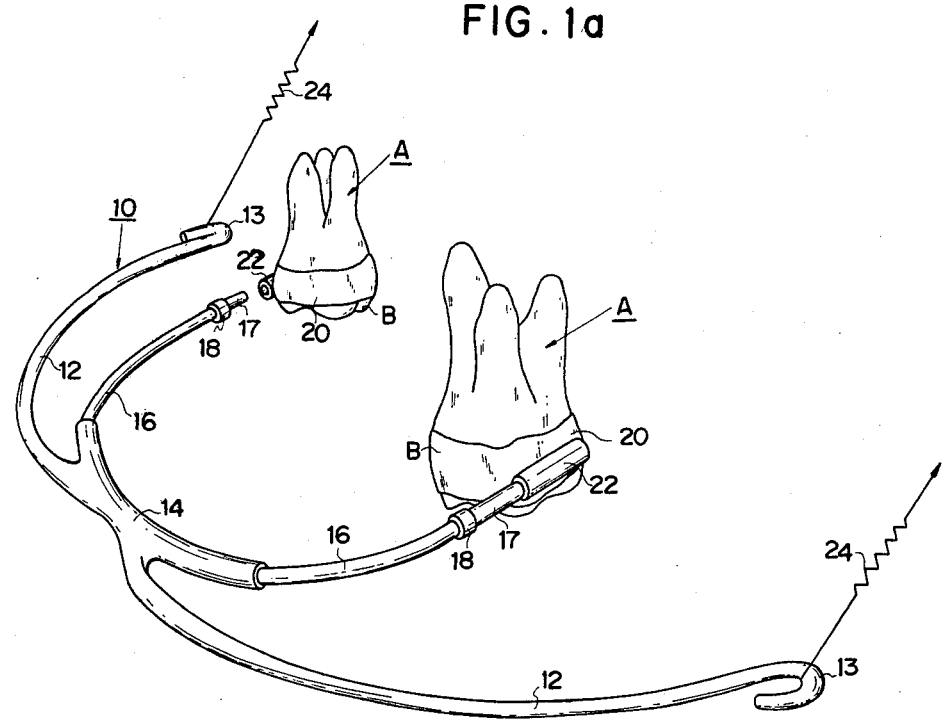
FIG. 1a and FIG. 1b are explanatory views for a prior art orthodontic device to which this invention may be applied.
Figure 1B:
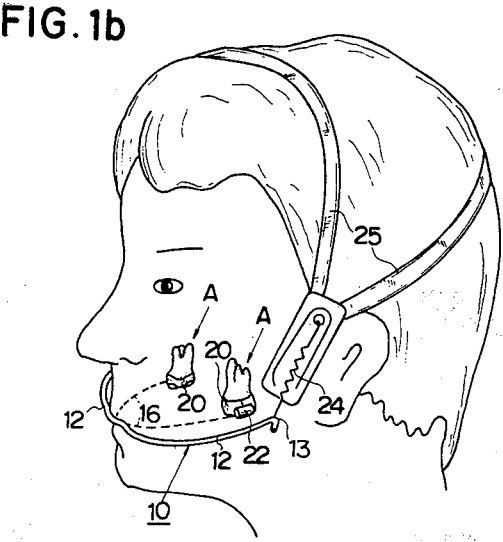

FIGS. 1a and 1b show a prior art typical orthodontic anchoring device as disclosed, for example, in U.S. Pat. No. 3,815,238. Reference numeral 10 identifies a face bow, 12 a pair of outer bow members each extending from a joint portion 14 and having at its free end a looped portion 13, and 16 a pair of inner bow members each also extending from the joint portion 14. The respective free ends 17 of the inner bows 16 are adapted to be inserted into respective metal buccal tubes 22 soldered at the buccal side to respective bands 20 engaged to and around the respective crown portions of the molars A. Reference numeral 18 identifies each of the stops for limiting the degree of insertion of the inner bow into the buccal tube 22. The cross section of the inner bow 16 is circular, and the buccal tube 22 and its hollow portion into which the end 17 of the inner bow is inserted have the substantially corresponding circular cross section.

The respective loops 13 at the free ends of the outer bows 12 each has a respective spring 24 connected thereto, the other ends of the respective springs 24 being connected to head gear 25, so that the outer bow 12 and hence the face bow 10 is adapted to be pulled from the direction of the head or neck portion (see FIG. 1b).

Figure 2A:
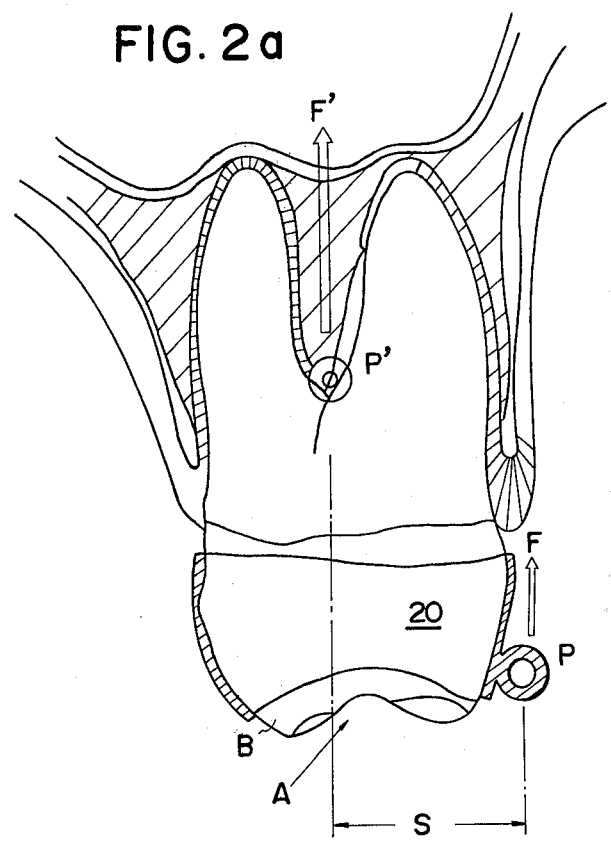
FIG. 2a and FIG. 2b are views for explaining the disadvantages of the prior art device shown by FIGS. 1a and 1b.
Figure 2B:
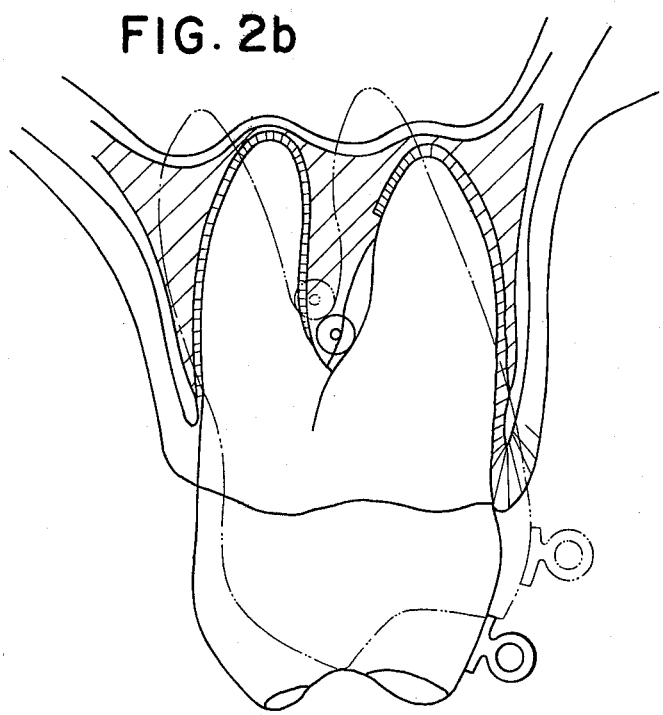

In these manners, the teeth and maxillary bone relating to the buccal tubes 22 receive a force in the direction of pulling of the face bow 10.

Where it is now desired to apply to the tooth A a force in the direction F' with respect to the point P' of center of resistance (this is created in response to the reaction of an alveolar bone and alveolar periosteum) for the purpose of orthodontic treatment, as is shown in FIG. 2a, and if a force in the direction F is applied to the tooth A with respect to the point P through the inner bow and buccal tube of the prior art anchoring device (incidentally, the forces F' and F are parallel with each other), it so results that the tooth A would be inclined as shown by a broken line in FIG. 2b although it is essentially desired to move the tooth A vertically upwards.

This is disadvantageous to other than a force system for forcibly imparting a rotation moment against the tooth for the purpose of some orthodontic treatment. Specially, in the case of the control of the maxillary bone through the teeth, since stresses are concentrated on the local portion around the tooth, there is the possibility of decreasing the efficiency.

The inventor found that such disadvantages of the prior art device are due mainly to such factors as of a distance S in the lateral direction between the point P' of center of resistance and the point P to which the actual force is applied, and circular cross sections of the inserted portion of the face bow and the inserting hollow portion of the buccal tube. Further, it was found that, of these factors, the influence resulting from the latter is greater.

Figure 3A:
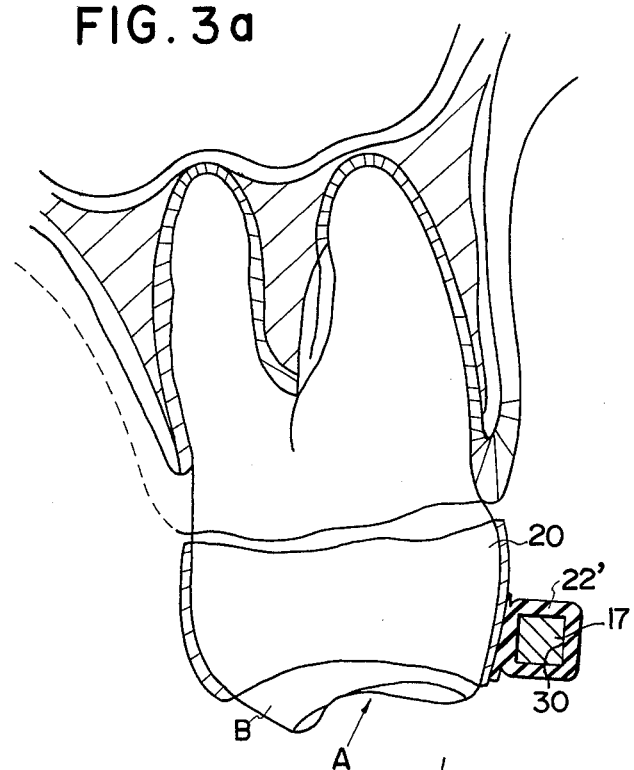
FIG. 3a and FIG. 3b are explanatory views for the embodiments of this invention.
Figure 3B:
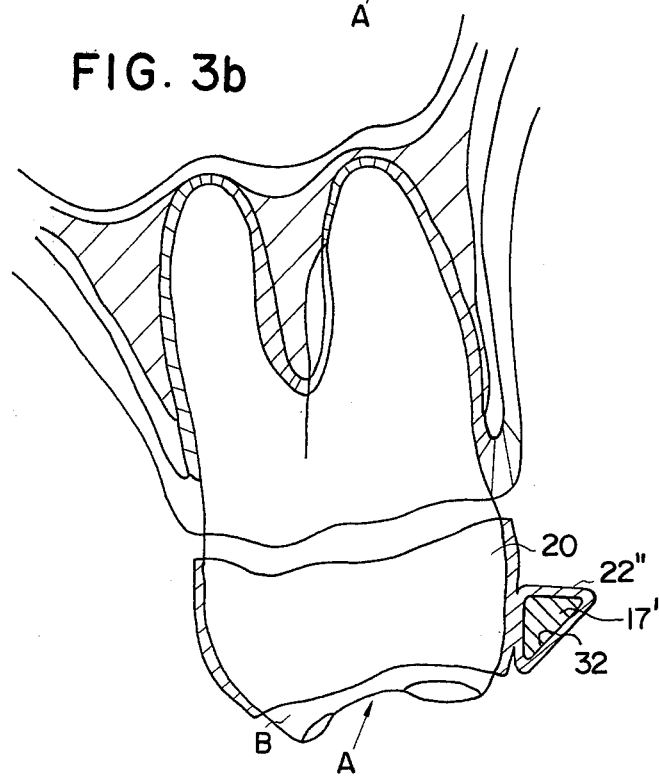

From the above, in order to impart to the molar such a force as not to provide any rotation moment, the cross section configuration of the hollow portion of the buccal tube and that of the inserted portion of the inner bow are designed to be shaped with a non-circular configuration (as shown in FIGS. 3a and 3b by the cross hatching 17 and 17'). That is to say, the cross section of the inserted portion of the inner bow is designed to be a shape other than a circle or having at least one angle along the length thereof, and the hollow portion of the buccal tube may be constructed in a corresponding cross section to that of the inner bow.

According to this invention, the disadvantages of the prior art device can be suitably overcome by shaping the inner bow and the buccal tube as mentioned above, and it becomes possible to efficiently use the force for pulling the face bow for the purpose of the orthopedic treatment.

FIGS. 3a and 3b show the configurations of the buccal tubes in the anchoring devices of this invention. The buccal tube 22 affixed to the band 20 may be modified to a hollow tube 22' with a quadrilateral cross section (FIG. 3a) or to a hollow tube 22" with a triangular cross section (FIG. 3b). The respective inner bow end with a corresponding cross section (not shown) is adapted to be inserted into the respective hollow portion 30, 32. In this invention, all configurations other than the circle, for example, a polygon and a partial circle are applicable as the cross section configuration of the inner bow and the buccal tube.

In this connection, it is to be noted that, for example, U.S. Pat. No. 1,322,944 discloses that a buccal tube is shaped in a non-circular configuration. However, this known art is directed only to a correction of a teeth alignment by engaging teeth with an arch wire threadedly received in a buccal tube without applying external forces to the teeth. This art, however, does never suggest an orthopedic technique as intended by the present invention wherein teeth are moved vertically by applying external forces through extraoral face bows. As mentioned above, the present invention provides an improvement in such a specific orthopedic technique and provides remarkable effects as demonstrated below.

Figure 4:
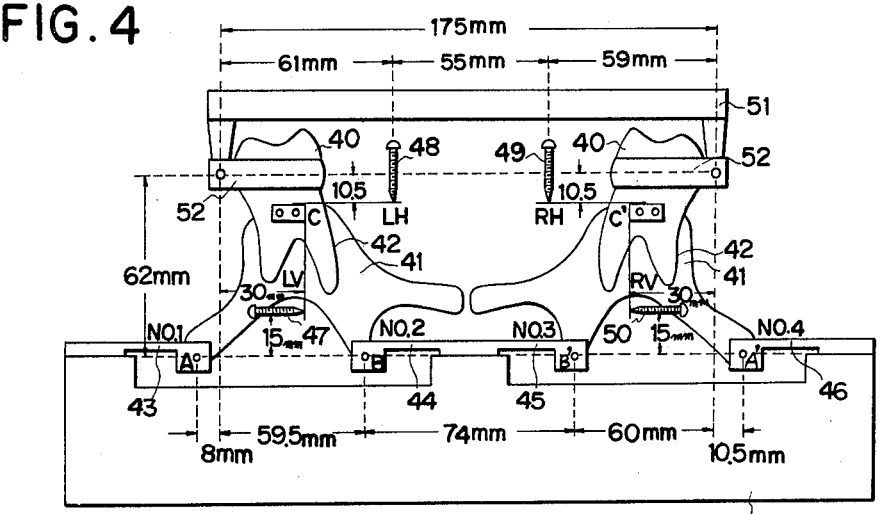
FIG. 4 is a diagram showing specifications of an experimental model for demonstrating the effects of the present invention.

FIG. 4 is a diagram showing specifications of an experimental model used for substantiating the effects of the present invention. Models of the maxillary first molars 40 and models of the maxillary bone 41 are made of a transparent acrylic board having a thickness of 6 mm. Ellastic filling material is used to fill the region of about 1 mm in width corresponding to the periodontal membrane 42. The maxillary bone is held by four brass cantilevers 43, 44, 45 and 46 each having a thickness of 3 mm, by one-point supporting at measuring points A, B, B' and A', respectively. The first molars 40 are fixed with two sets of phosphorus bronze cantilevers LV and LH, and RV and RH each having a thickness of 0.5 mm. The cantilevers of each set are connected at right angles to each other at C and C', respectively, and having free ends contacting with tips of fixing bolts 47, 48, 49 and 50 inserted from the external sides for calibration operation.

In the figure, 51 is a model of an inner bow and 53 is a cantilever supporting table. 52 designates models of buccal tubes anchored to the respective molar models 40 and connected at respective ends to the inner bow model 51.

In experiments, the buccal tube and inner tube in accordance with the present invention as specified above were fixed, and the tips of the external fixing bolts 47 to 50 were advanced forwardly by 2 mm from the positions where they contacted the cantilevers so as to bend the cantilevers. This facilitates the measurement of the displacements of C and C' in the upper first molars in either the correct or opposite direction.

After the above-mentioned settings had been completed, loadings were applied to the center of the inner bow model 51 from 200 g [including the 100 g weight of the apparatus (not shown) itself] up to 1200 g, and the mean values of five measurements at each level were obtained.

Whereas, in the cases of cantilevers Nos. 1, 2, 3 and 4 (+) was marked when depression was observed, in the cases of cantilevers LH and RH, (+) was marked when C and C' in the upper first molars were displaced downward; that is, when the cantilever returned to the upposition. In the cases of LV and RV, on the other hand, (+) was marked when point C and point C' were displaced outwardly, that is, when the cantilever returned to the inner position.

Removing the inner bow model 51, loading was done on only one of the first molars. The loading points were eight points set at 5 mm intervals from the basal point on the buccal tube model 52 to a point 35 mm distant in the direction of a palatal side.

Because the weight of the loading apparatus was 39 g, loads from 135 g to 639 g were applied, adding 100 g each time. By repeating the experiment five times at each loading point, mean values of the measurements were obtained.

Figure 5:
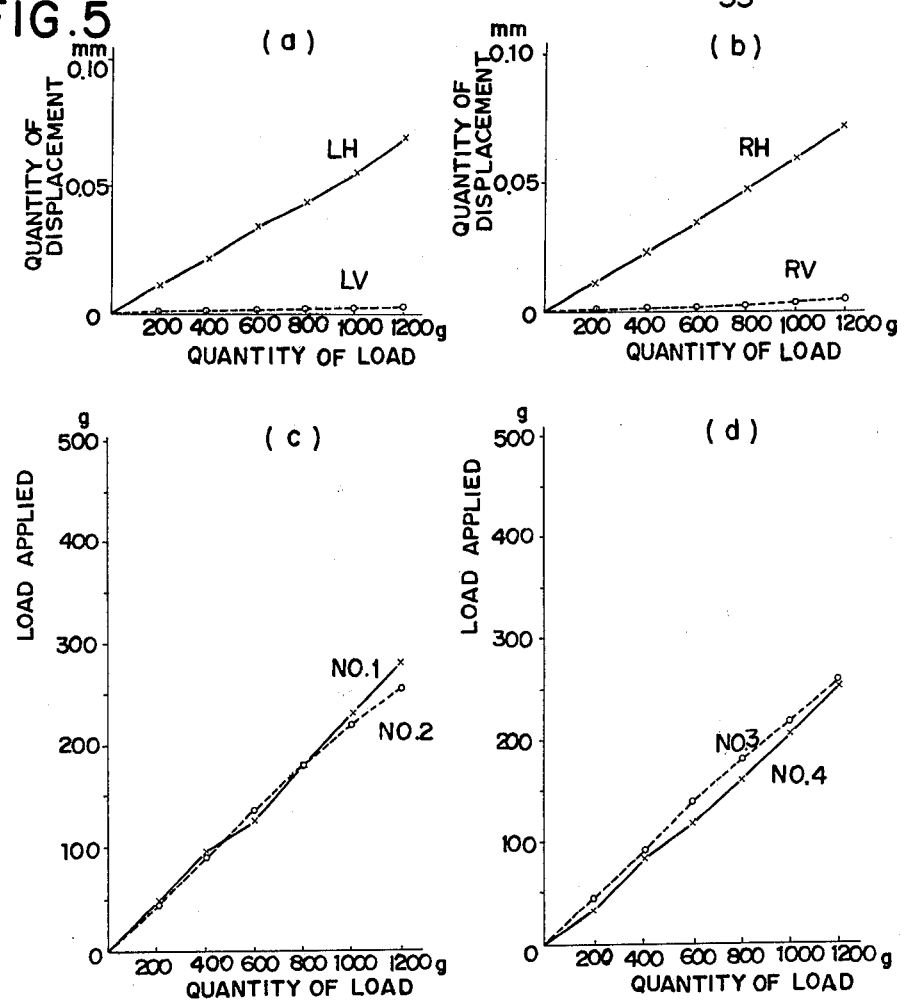
FIG. 5 is graphs showing the measured results obtained by the experimental model illustrated in FIG. 4.

According to the results of the above-mentioned experiments, while the displacements of the cantilevers LH and RH in the upper first molar models 40 showed increases in proportion to the increase in the amount of the load applied (0.0693 mm and 0.0719 mm, respectively, at 1200 g), those of the cantilevers LV and RV showed little increase with the increasing load being only 0.0029 mm and 0.0041 mm respectively, at 1200 g (see the table given below and FIG. 5 (a) and (b)).

In the maxillary bone model 41, the load borne by the cantilevers showed approximately the same rates of increase with the increases in the amount of the load given. At the loading of 1200 g, they were 280.00 g, 254.31 g, 259.88 g and 252.80 g, respectively, as summarized in the following table and shown in FIG. 5 (c) and (d).

TABLE

| cantilever unit load | No. 1 (g) | No. 2 (g) | LH (mm) | LV (mm) | RV (mm) | RH (mm) | No. 3 (g) | No. 4 (g) |
|---|---|---|---|---|---|---|---|---|
| 200g | 46.40 | 41.44 | 0.0112 | 0.0003 | 0.0006 | 0.0113 | 43.88 | 34.56 |
| 400g | 96.00 | 91.81 | 0.0216 | 0.0010 | 0.0008 | 0.0230 | 92.25 | 84.93 |
| 600g | 125.60 | 134.88 | 0.0347 | 0.0015 | 0.0016 | 0.0347 | 141.75 | 118.50 |
| 800g | 178.40 | 177.94 | 0.0439 | 0.0020 | 0.0020 | 0.0475 | 180.00 | 161.95 |
| 1000g | 230.40 | 220.19 | 0.0554 | 0.0023 | 0.0036 | 0.0595 | 218.25 | 205.40 |
| 1200g | 280.00 | 254.31 | 0.0693 | 0.0029 | 0.0041 | 0.0719 | 259.88 | 252.80 |

Figure 6:
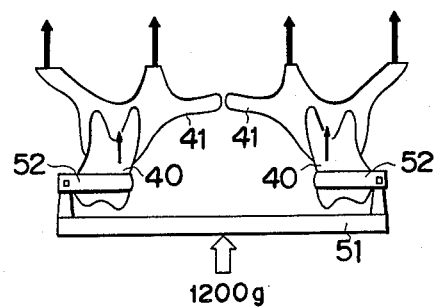
FIG. 6 is a diagram for explaining the effects of the experimental model illustrated in FIG. 4.

It can be seen from the results of the experiments that while the cantilevers LH and RH showed the displacements of 0.0693 mm and 0.0719 mm, respectively, those of LV and RV were only 0.0029 mm and 0.0041 mm, respectively, and the upper first molars were almost vertically depressed. Furthermore, the loads borne by cantilevers No. 1 through No. 4 were approximately equal, being 280.00 g, 254.31 g, 259.88 g and 252.80 g, respectively (see FIG. 6). It is further substantiated that the loadings by the buccal tube and the inner bow according to the present invention can reduce a rotation of the upper first molar and the maxillary bone towards a buccal side as compared with the conventional buccal tube and inner bow.

Figure 7:
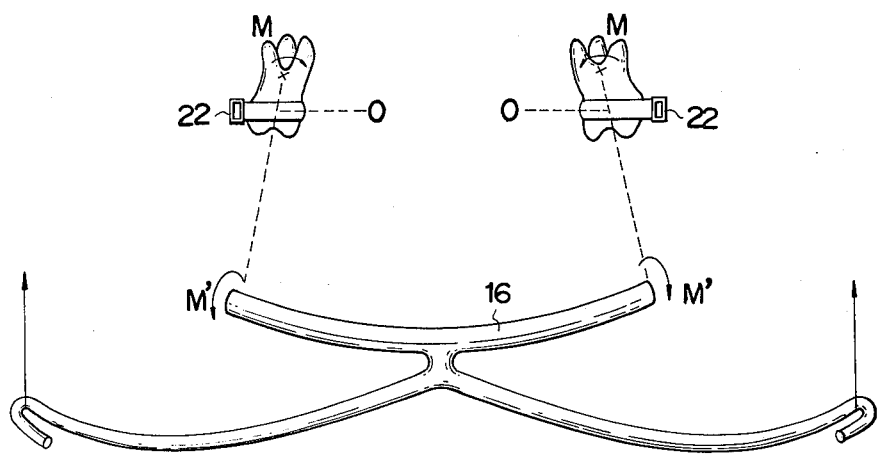
FIG. 7 is a schematic view showing the reverse moments M' applied to the inner bows by twisting the same prior to their insertion into the buccal tubes.

In the embodiment of the present invention as mentioned above, the inner bow 16 may preliminarily be rotated or twisted inwardly before it is inserted into the buccal tube 22. In this case, when a vertical traction is carried out, a reverse rotation moment M' (see FIG. 7) is exerted for cancelling a moment between resistance center of the tooth and the buccal tube. Thus, the rotation towards the buccal side is more effectively depressed.

I claim:

1. In combination, a head harness for exerting an upward force; a pair of buccal tubes adapted to be connected to the molar teeth on the opposite sides of a human mouth and to which a vertical force is to be imparted; an extra-oral anchorage device for imparting an orthopedic force vertically to said molar teeth comprising a face bow including outer bows adapted to extend along the opposite cheeks of the user and connected to said head harness; an inner bow connected to each outer bow and having an outer free end inserted into the associated buccal tube to transmit the force applied by said harness thereto, each inner bow inserted in its associated buccal tube, means for preventing rotation of the inner bow within the buccal tube, and each inner bow being rotated or twisted about its longitudinal axis so as to impart a reverse rotation moment which substantially cancels a moment produced between each buccal tube and the resistance center of the associated tooth by said upward force transmitted thereto, whereby the orthopedic forces substantially parallel to the vertical axes of the molar teeth can be transmitted without imparting an undesired rotational moment to the teeth.

2. The combination of claims 1, wherein the outer free end of each inner bow has a non-circular cross section and the associated buccal tube has a shape and size corresponding to said non-circular outer free end of said inner bow so as to receive and closely encircle said outer free end of the inner bow on all sides thereof, to prevent rotation thereof in the buccal tube.

* * * * *

UNITED STATES PATENT AND TRADEMARK OFFICE
CERTIFICATE OF CORRECTION

PATENT NO. : 4,378,210

DATED : March 29, 1983

INVENTOR(S) : Kenichi Yatabe

It is certified that error appears in the above-identified patent and that said Letters Patent is hereby corrected as shown below:

On the title page delete (73) Asignee:
"Clarion Co., Ltd., Tokyo, Japan"

Signed and Sealed this

Eighth Day of November 1983

[SEAL]

*Attest:*

GERALD J. MOSSINGHOFF

*Attesting Officer*  *Commissioner of Patents and Trademarks*